(12) United States Patent
Baker et al.

(10) Patent No.: US 6,242,658 B1
(45) Date of Patent: Jun. 5, 2001

(54) PROCESS FOR THE MANUFACTURE OF FLUORINE-SUBSTITUTED HYDROCARBONS

(75) Inventors: Ralph Thomas Baker, Los Alamos, NM (US); Richard Paul Beatty, Wilmington, DE (US); Allen Capron Sievert, Elkton, MD (US); Robert Lewis Wallace, Jr., Wilmington, DE (US)

(73) Assignee: E. I. duPont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/155,262

(22) PCT Filed: Mar. 25, 1997

(86) PCT No.: PCT/US97/04801

§ 371 Date: Aug. 6, 1999

§ 102(e) Date: Aug. 6, 1999

(87) PCT Pub. No.: WO97/35820

PCT Pub. Date: Oct. 2, 1997

Related U.S. Application Data

(60) Provisional application No. 60/014,351, filed on Mar. 28, 1996.

(51) Int. Cl.$^7$ ............................. C07C 19/08; C07F 15/00
(52) U.S. Cl. ........................... 570/124; 556/13; 558/460; 558/461; 560/227
(58) Field of Search .................... 570/124; 560/227; 556/13; 558/430, 461

(56) References Cited

U.S. PATENT DOCUMENTS

| | | |
|---|---|---|
| 3,022,356 | 2/1962 | Ver Nooy, III . |
| 3,355,498 | 11/1967 | Pascal et al. . |
| 4,012,399 | 3/1977 | Hechenbleikner et al. . |
| 5,194,170 | 3/1993 | Merchant et al. . |
| 5,221,493 | 6/1993 | Merchant et al. . |
| 5,250,208 | 10/1993 | Merchant et al. . |
| 5,545,769 | 8/1996 | Baker et al. . |

FOREIGN PATENT DOCUMENTS

| | | |
|---|---|---|
| WO 92/06941 | 4/1992 | (WO) . |
| WO 95/19947 | 7/1995 | (WO) . |
| WO 96/10002 | 4/1996 | (WO) . |

OTHER PUBLICATIONS

J.G. Verkade et al., Transition Metal Complexes of a Constrained Phosphite Ester. III. Metal Carbonyl Complexes of 4–Methyl–2,6,7–trioxa–1–phosphabicyclo[2.2.2]octaine, *Inorganic Chemistry*, 4, No. 2, 228–231, Feb. 1965.

C.A. Tolman et al., Reactions of Cyanogen with Zerovalent Nickel Complexes, *Inorganic Chemistry*, 16, No. 4, 940–943, Apr. 1977.

*Primary Examiner*—Paul J. Killos

(57) ABSTRACT

Processes involving certain nickel metallacycles with phosphite ligands are disclosed as useful for the manufacture of selected substituted hydrocarbons. Also disclosed are selected compounds including both nickel and phosphite ligands.

6 Claims, No Drawings

PROCESS FOR THE MANUFACTURE OF FLUORINE-SUBSTITUTED HYDROCARBONS

This application represents a national filing under 35 USC 371 of International Application No. PCT/US97/04801 filed Mar. 25, 1997 and claims priority benefit of U.S. Provisional Application Ser. No. 60/014,351 filed Mar. 28, 1996.

FIELD OF THE INVENTION

This invention relates to processes for producing selected substituted hydrocarbons containing fluorine, and more particularly to processes involving hydrogenolysis for producing substituted hydrocarbons containing fluorine and hydrogen and compositions provided in such processes.

BACKGROUND OF THE INVENTION

Chlorofluorocarbons (CFCs, i.e., compounds containing only carbon, fluorine and chlorine) have been used for many years as refrigerants, heat transfer media, foam expansion agents, aerosol propellants, solvents and power cycle working fluids. For example, various CFC solvents have been used as cleaning liquids for the removal of contaminants from contaminated articles and materials. Certain fluorine-containing organic compounds such as 1,1,2-trichloro-1,2,2-trifluoroethane (CFC-113) have been reported as useful for this purpose, particularly with regard to cleaning organic polymers and plastics which may be sensitive to other more common and more powerful solvents such as trichloroethylene or perchloroethylene. Recently, however, there have been efforts to reduce the use of certain chlorofluorocarbon compounds such as CFC-113 because of a concern over their potential to deplete ozone, and to thereby affect the layer of ozone that is considered important in protecting the earth's surface from ultraviolet radiation. Consequently, there is a worldwide effort to find alternative compounds which contain fewer or preferably no chlorine substituents.

Boiling point, flammability and solvent power can often be adjusted by preparing mixtures of solvents. For example, certain mixtures of 1,1,2-trichloro-1,2,2-trifluoroethane with other solvents (e.g., isopropanol and nitromethane) have been reported as useful in removing contaminants which are not removed by 1,1,2-trichloro-1,2,2-trifluoroethane alone, and in cleaning articles such as electronic circuit boards where the requirements for a cleaning solvent are relatively stringent (i.e., it is generally desirable in circuit board cleaning to use solvents which have low boiling points, are non-flammable, have low toxicity, and have high solvent power so that flux such as rosin and flux residues which result from soldering electronic components to the circuit board can be removed without damage to the circuit board substrate).

While boiling point, flammability, and solvent power can often be adjusted by preparing mixtures of solvents, the utility of the resulting mixtures can be limited for certain applications because the mixtures fractionate to an undesirable degree during use. Mixtures can also fractionate during recovery, making it more difficult to recover a solvent mixture with the original composition. Azeotropic compositions, with their constant boiling and constant composition characteristics, are thus considered particularly useful.

The properties of halogenated hydrocarbons can be influenced by the arrangement of the halogens (and hydrogen, when present) on the carbon framework. One of the challenges in preparing compounds containing fluorine and hydrogen has been achieving the desired arrangement of such substituents.

One arrangement involves providing a hydrogen on different carbons spaced a selected distance from one another along a carbon chain. For example, it can be desirable to provide a hydrogen substituent on each of two carbon atoms which are separated from one another by a chain of two other carbon atoms. 1,1,2,2,3,3,4,4-Octafluorobutane (HFC-338pcc) is such a compound. HFC-338pcc forms useful blends, and particularly azeotropes, with solvents such as alcohols, ketones, and other halogenated solvents to form compositions useful for cleaning surfaces, especially electronic components as disclosed in U.S. Pat. No. 5,250,208, U.S. Pat. No. 5,221,493, and U.S. Pat. No. 5,194,170. There is a need for non-chlorinated solvents like HFC-338pcc (which have little effect on the ozone layer) as replacements for more chlorinated solvents such as CFC-113. There is also a need for processes for effectively producing compounds such as HFC-338pcc.

U.S. patent application Ser. No. 08/315,025 (the priority document for PCT International Publication No. WO 96/10002), which is incorporated herein by reference, discloses a process for the preparation of product compounds of the formula $HC(R^1)_2C(R^1)_2C(R^2)_2C(R^2)_2H$ (e.g., $CHF_2CF_2CF_2CHF_2$, HFC-338pcc) by reaction of a metallacycle of the formula

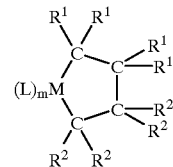

with hydrogen.

SUMMARY OF THE INVENTION

The present invention provides an advantageous process for the manufacture of a product compound of the formula $HC(R^1)_2C(R^1)_2C(R^2)_2C(R^2)_2H$ wherein each $R^1$ is independently selected from the group consisting of H, F, Cl, CN, R, OR, $CO_2R$, $C(O)R$, $OC(O)R$, $R^f$, $OR^f$, $CO_2R^f$ $C(O)R^f$ and $OC(O)R^f$, where R is a hydrocarbyl group and $R^f$ is a $C_1$ to $C_{10}$ polyfluoroalkyl group, provided that at least one $R^1$ is F, and wherein each $R^2$ is independently selected from the group consisting of H, F, Cl, CN, R, OR, $CO_2R$, $C(O)R$, $OC(O)R$, $R^f$, $OR^f$, $CO_2R^f$ $C(O)R^f$, $OC(O)R^f$ and difunctional linkages where an $R^2$ on each of two adjacent carbon atoms together form a link selected from the group consisting of —$CH_2CH_2CH_2$—, —$CH_2CH_2CH_2CH_2$—, —$CH_2CH_2CH(CH_3)$—, —$CH_2CH(CH_3)CH_2$—, —C(O)OC(O)—, and norborndiyl.

The process of this invention comprises reacting a metallacycle of the formula

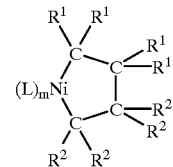

(i.e., $L_mNi(1,4$—$C(R^1)_2C(R^1)_2C(R^2)_2C(R^2)_2$—)) wherein $R^1$ and $R^2$ are as defined above, and wherein each L is a ligand independently selected from the group consisting of a phosphite of the formula $P(OR^3)_3$,

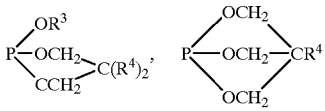

and $(R_3O)_2POP(OR_3)_2$; each $R^3$ is independently selected the group consisting of $CH_2CR^6R^7R^8$; each $R^6$, $R^7$, and $R^8$ is independently selected from the group consisting of $C_1$ to $C_{10}$ alkyl, benzyl, phenyl, and phenyl substituted with one or more $R^{10}$, provided that two of $R^6$, $R^7$, and $R^8$ in a $R^3$ may be co-joined to provide a $C_5$ to $C_7$ cycloalkane ring, and that all three of $R^6$, $R^7$, and $R^8$ in a $R^3$ may together form an adamantyl group; each $R^{10}$ is independently selected from the group consisting of $C_1$ to $C_4$ alkyl, F, Cl, Br, $N(R^9)_2$, $OR^9$ and $CO_2R^9$; each $R^9$ is independently selected from the group consisting of H and $C_1$ to $C_4$ alkyl; each $R^4$ is independently selected from the group consisting of $C_1$ to $C_4$ alkyl; and m is an integer from 1 to 2, with hydrogen.

This invention also provides metallacyclic compounds, for example, a compound of the formula $L_2Ni(1,4—CR^1_2CR^1_2CR^2_2CR^2_2—)$ wherein L, $R^1$ and $R^2$ are as defined above.

This invention also provides nickel compounds, for example, a compound of the formula $L_4Ni$ wherein L is as defined above.

DETAILED DESCRIPTION

A metallacycle is a cyclic carbon compound where one or more carbons are replaced by a transition metal. Applicants have discovered that certain fluorine-containing nickel metallacycles can be advantageously reacted with hydrogen to add hydrogen to each of two carbon atoms separated from one another by a chain of two other carbon atoms and produce selected halogenated hydrocarbons containing fluorine and hydrogen.

An olefinic compound of the formula $(R^1)_2C=C(R^1)_2$ and another or the same olefinic compound of the formula $(R^2)_2C=C(R^2)_2$ may be reacted in the liquid phase with a nickel complex of the formula $NiL_n$ where n is an integer from 2 to 4 to form a metallacycle of the structure shown in the Summary of the Invention. In accordance with this invention, the metallacycle may be reacted in the liquid phase with hydrogen to produce an organic compound of the formula, $HC(R^1)_2C(R^1)_2C(R^2)_2C(R^2)_2H$. The nickel fragment $NiL_m$ released by the hydrogenation reaction, which under the reaction conditions may revert partly or completely to $NiL_n$, typically may be converted back to the metallacyclic compound, $NiL_m(1,4—C(R^1)_2C(R^1)_2C(R^2)_2C(R^2)_2—)$, by subsequent reaction with the olefinic compounds $(R^1)_2C=C(R^1)_2$ and $(R^2)_2C=C(R^2)_2$. Each $R^1$ and $R^2$ may be independently selected from the group consisting of H, F, Cl, CN, OR, $CO_2R$, C(O)R, OC(O)R, $R^f$, $OR^f$, $CO_2R^f$, $C(O)R^f$, and $OC(O)R^f$, (provided that at least one $R^1$ is F). Also, one $R^2$ group on each of two adjacent carbons may together form a link selected from the group consisting of $—CH_2CH_2CH_2—$, $—CH_2CH_2CH_2CH_2—$, $—CH_2CH_2CH(CH_3)—$, $CH_2CH(CH_3)CH_2—$, $—C(O)OC(O)—$, and norborndiyl (i.e.,

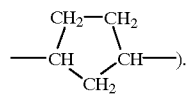

R is a hydrocarbyl group. By hydrocarbyl is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include, for example, methyl, ethyl, propyl, isopropyl, butyl, isobutyl, t-butyl, cyclopropyl, cyclobutyl, cyclopentyl, methylcyclopentyl, cyclohexyl, methylcyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl. $R^f$ is a polyfluoroalkyl group having from 1 to 10 carbon atoms. Examples of suitable polyfluoroalkyl groups include, for example, $—CH_2F$, $—CHF_2$, $—CF_3$, $—CH_2CF_3$, $—CF_2CHF_2$, $—C_2F_5$, $—CH_2CF_2CHF_2$, $—CH_2C_2F_5$, $—CH_2CH_2C_2F_5$, $—CF_2CHFCF_3$, $—CF_2CF_2CF_2CHF_2$, $—CH_2CF_2CF_2CF_2CHF_2$, $—CF_2CF_2CF_2CF_3$, and $—CH_2CH_2CF_2CF_2CF_2CF_3$. Preferably each $R^1$ is selected from the group H, Cl, F, CN, and $OCF_3$ (provided, as noted above, that at least one $R^1$ is F). Of note are embodiments where at least two $R^1$ groups are F and embodiments where at least three of the $R^1$ groups are selected from Cl or F. Preferably each $R^2$ is independently selected from the group H, Cl, F, CN, $OCF_3$, $C_6H_5$, $CF_3$ and $CO_2CH_3$.

Examples of olefins of the formula $(R^1)_2C=C(R^1)_2$ include, perfluorocyclobutene (i.e., $C_4F_6$), perfluorocyclopentene (i.e., $C_5F_8$) $CF_2=CF_2$, $CF_2=CFCl$, $CF_2=CCl_2$, $CFCl=CFCl$, $CFCl=CCl_2$, $CF_2=CFH$, $CF_2=CH_2$, $CFH=CFH$, $CFH=CH_2$, $CF_2=CF(CN)$, $CF_2=C(CN)_2$, $CF(CN)=CF(CN)$, $CF(CN)=C(CN)_2$, $CF_2=CFCF_3$, $CF_2=CHCF_3$, $CF_3CF=CHF$, $CF_2=CFCF_2CF_3$, $CF_2=CFCF_2CF_2CF_2CF_3$, $CF_2=CFCH_3$, $CF_2=CF(C_6H_5)$, $CF_2=CF(C_6F_5)$, $CF_2=CFOCH_3$, $CF_2=CFOCH_2F$, $CF_2=CFOCHF_2$, $CF_2=CFOCF_3$, $CF_3CF_2OCF=CF_2$, $CF_2=CHOCF_2CHF_2$, $CF_2=CFOCF_2CF_2CF_3$, $CF_2=CFCO_2CH_2CH_3$, and $CF_2=CFCO_2CF_2CF_3$. Examples of olefins of the formula $(R^2)_2C=C(R^2)_2$ include those exemplified for the formula $(R^1)_2C=C(R^1)_2$, as well as $CH_2=CH_2$, $CH_2=CHCH_3$, $CH_2=CHCF_3$, $CH_2=CHCH_2CH_3$, $CH_2=CHCF_2CF_3$, $CH_2=CHOCH_3$, $CH_2=CHOCF_3$, $CH_2=CHOC(O)CH_3$, $CH_2=CHOC(O)CF_3$, $CH_2=CHCO_2CH_3$, $CH_2=CHCO_2CF_3$, $H_3CO_2CCH=CHCO_2CH_3$, $CH_2=CHCl$, $CH_2=CCl_2$, $CHCl=CHCl$, $CHCl=CCl_2$, $CH_2=CHCF_3$, $CH_2=CHOCF_3$, $CH_2=CHC_6H_5$, $CH_2=CHCl$, $CH_2=CHF$, $CH_2=CH(CN)$, $CH(CN)=CH(CN)$, HC (CN) $=CHCH_2CH_2CN$, cyclopentene, methylcyclopentenes, cyclohexene, norbornene, and maleic anhydride. Preferred olefins of the formula $(R^1)_2C=C(R^1)_2$ include $CF_2=CF_2$, $CF_2=CFCl$, $CF_2=CFH$, $CF_2=CF(CN)$, $CF_2=CFOCF_3$, and $CF_2=CFCO_2CF_2CF_3$. Preferred olefins of the formula $(R^2)_2C=C(R^2)_2$ include those preferred for the formula $(R^1)_2C=C(R^1)_2$, as well as, $CH_2=CH_2$, $CH_2=CHCF_3$, $CH_2=CHOCF_3$, $CH_2=CHC_6H_5$, $CH_2=CHF$, $CH_2=CHCl$, $CH_2=CHCN$, and $CH_2=CHCO_2CH_3$. Of note are embodiments wherein each $R^1$ and $R^2$ is either H or F. Also of note are embodiments where the first olefinic reactant is the same as the second olefinic reactant (e.g., both are $CF_2=CF_2$). Especially preferred for the process of this invention is $CF_2=CF_2$.

While U.S. patent application Ser. No. 08/315,025 discloses that a wide range of ligands may be useful to prepare the metallacycles, the present invention involves a preferred class ligands which provide the desired nickel metallacycles and product compounds $HC(R^1)_2C(R^1)_2C(R^2)_2C(R^2)_2H$ in high yield and selectivity.

Examples of ligands of the type $P(OR^3)_3$ include $P(OCH_2C(C_2H_5)_2(CH_3))_3$, $P(OCH_2C(CH_3)_2(C_5H_{11}))_3$, $P(OCH_2C(CH_3)_2(C_4H_9))_3$, $P(OCH_2C(C_2H_5)_3)_3$, $P(OCH_2C(C_2H_5)_2(C_3H_7))_3$, $P(OCH_2C(CH_3)_3)_3$, $P(OCH_2C(CH_3)_2(C_2H_5))_3$, $P(OCH_2C(CH_3)_2(C_3H_7))_3$, $P(OCH_2C(CH_3)_2(C_6H_5))_3$, $P(OCH_2C(CH_3)_2(CH_2C_6H_5))_3$, and $P(OCH_2(adamantyl))_3$. Examples of ligands of the type $P(OR^3)(OCH_2)_2C(R^4)_2$ include $P(OCH_2C(CH_3)_3)(OCH_2C(CH_3)_2CH_2O)$, $P(OCH_2C(CH_3)_3)(OCH_2C(C_2H_5)_2CH_2O)$, $P(OCH_2C(CH_3)_2(CH_2C_6H_5))(OCH_2C(CH_3)(C_3H_7)CH_2O)$, and $P(OCH_2C(CH_3)_2(C_3H_7))(OCH_2C(C_2H_5)(C_4H_9)CH_2O)$. Examples of ligands of the type $P(OCH_2)_3CR^4$ include $P((OCH_2)_3CCH_3)$ and $P((OCH_2)_3CC_2H_5)$. An example of a ligand of the type $(R^3O)_2POP(OR^3)_2$ is $((CH_3)_3CCH_2O)_2POP(OCH_2C(CH_3)_3)_2$. Other examples of phosphite ligands include 2,2'-((2,2-dimethyl-1,3-propanediyl)bis(oxy))bis(5,5-dimethyl 1,3,2-dioxaphosphorinane (CAS Registry No. 59609-05-1) and 4,4'-(oxybis(methylene))bis-2,6,7-trioxa-1-phospha-bicyclo (2.2.2)octane (CAS Registry No. 17013-79-5).

Trineopentyl phosphite (that is, $P(OCH_2C(CH_3)_3)_3$) is considered especially useful in combination with Ni, and $Ni(P(OCH_2C(CH_3)_3)_3)_4$ (i.e., n is 4) is an especially useful metal complex for preparing nickel metallacycles. Of note are embodiments where the metallacycle is reacted with hydrogen in the presence of trineopentyl phosphite and the metal complex (e.g., a metal complex of Ni and trineopentyl phosphite) is produced along with the product compound.

The phosphites described above may be prepared by techniques known in the art such as those described by G. M. Kosolapoff in chapter eight of *Organophosphorous Compounds* (John Wiley & Sons: New York, 1950). A general scheme for the formation of such phosphites is the reaction of $PCl_3$ with the corresponding alcohol with or without the presence of a base catalyst.

Of particular note are phosphites having one of the neopentyl structures, $P(OCH_2C(CH_3)_2(R^5))_3$, or $P(OCH_2C(C_2H_5)_2R^5)_3$ wherein $R^5$ is $C_1$ to $C_8$ alkyl (e.g., methyl, ethyl, or propyl). These phosphites are advantageously derived from the corresponding alcohols, $HOCH_2C(CH_3)_2(R^5)$ and $HOCH_2C(C_2H_5)_2R^5$, which may in turn be obtained by reduction of the commercially available carboxylic acids, $HOC(O)C(CH_3)_2(R^5)$ and $HOC(O)C(C_2H_5)_2R^5$, or mixtures of the carboxylic acids. Suitable means of reduction include the use of hydrogen at elevated temperature and pressure in the presence of a catalyst or by means of hydridic reducing agents such as lithium aluminum hydride. Similar reductions of acid derivatives such as esters, $R^5OC(O)C(CH_3)_2(R^5)$ and $R^5OC(O)C(C_2H_5)_2R^5$, or acid chlorides, $ClC(O)C(CH_3)_2(R^5)$ and $ClC(O)C(C_2H_5)_2R^5$, may also be used to advantage.

The preferred metal complexes for preparing metallacycles for the process of this invention are generally zero-valent nickel complexes of the type $NiL_4$ or $NiL_3$ where each L may be independently selected from the ligands disclosed above. The $NiL_4$ or $NiL_3$ metal complexes may be pre-formed or prepared in situ from suitable nickel precursors.

An especially preferred group of nickel complexes has the general formula $NiL_4$ or $NiL_3$ where each L is independently selected from those having the formula $P(OR_3)_3$ wherein the $R^3$s may be the same or different. An especially preferred ligand is trineopentylphosphite, $P(OCH_2C(CH_3)_3)_3$. Under many of the reaction conditions one or more of L ligands may become disassociated from the nickel.

Zero-valent nickel complexes can be prepared or generated according to techniques well known in the art (see, e.g., U.S. Pat. No. 3,496,217, U.S. Pat. No. 3,631,191, U.S. Pat. No. 3,846,461, U.S. Pat. No. 3,847,959, U.S. Pat. No. 3,903,120, and Tolman, et al. *J. Am. Chem. Soc.* Vol. 96, page 2774 (1974). Zero-valent nickel compounds that contain ligands which can be displaced by the organophosphorus ligand are a preferred source of zero-valent nickel. Two such preferred zero-valent nickel compounds are $Ni(COD)_2$ (where COD is 1,5-cyclooctadiene) and $Ni(P(O-o-C_6H_4CH_3)_3)_2(C_2H_4)$, both of which are known in the art (see, e.g., Seidel et al., *Inorg. Chem.,* 1970, Vol. 9, p. 2354 and S. D. Ittel, *Inorganic Synthesis,* Vol. 17, 1977, pp. 117–124 and Vol. 28, 1990, pp. 98–104). Alternatively, divalent nickel compounds may be combined with a reducing agent, and are then able to serve as suitable sources of zero-valent nickel in the reaction. Suitable divalent nickel compounds include compounds of formula $NiY_2$, where Y is halide, carboxylate, or acetylacetonate. Suitable reducing agents include metal borohydrides, metal aluminum hydrides, metal alkyls, Zn, Fe, Al, Na, or $H_2$. Elemental Ni, preferably nickel powder, when combined with a halogenated catalyst, as described in U.S. Pat. No. 3,903,120, is also a suitable source of zero-valent nickel.

The solvent used for the preparation of the metallacycle and hydrogenolysis of the metallacycles of this invention should be liquid at the reaction temperature and pressure, should not exert any deleterious effect towards the olefinic reactants or the metallacycle, and should have the property of dissolving a sufficient amount of metal complex and metallacycle to react with olefinic compounds and hydrogen, respectively.

Suitable solvents include cyclic or acyclic hydrocarbons (e.g., pentane, cyclopentane, hexanes, cyclohexane, mineral spirits, or kerosene), aromatic hydrocarbons (e.g., benzene, chlorobenzene, toluene, xylene, mesitylene, or tetralin), nitriles (e.g., acetonitrile, valeronitrile, benzonitrile or adiponitrile), ethers (e.g., diethyl ether, methyl t-butyl ether, 1,2-dimethoxyethane, tetrahydrofuran or dioxane), ketones (e.g., acetone), esters (e.g., dimethyl carbonate, methyl acetate or methyl formate) or polar organic solvents (e.g., dimethyl sulfoxide, N,N-dimethyl formamide, pyridine, N-ethyl-morpholine, isopropanol, and sulfolane). Mixtures of the above solvents may also be employed to advantage.

In many cases, the ligand, L, may serve as at least part (i.e., part or all) of the solvent. The presence of ligand during hydrogenolysis may be particularly advantageous in stabilizing the metal fragment liberated as a result of hydrogenolysis of the metallacycle. In other cases, the olefin, $(R^2)_2C=C(R^2)_2$, may serve as at least part (i.e., part or all) of the solvent. Of note are embodiments wherein the solvent is the product of the hydrogenolysis of the metallacycle, $HC(R^1)_2C(R^1)_2C(R^2)_2C(R^2)_2H$.

In one embodiment of this invention the metallacycle is prepared in a separate step by contacting a metal complex of the type $NiL_n$ dissolved in a suitable solvent, as defined above, with an olefinic compound of the formula $(R^2)_2C=C(R^2)_2$ and another or the same olefinic compound of the formula $(R^1)_2C=C(R^1)_2$, where $R^1$ and $R^2$ are as defined above. Typically, the reaction is accomplished at temperatures from −25 to 200° C., at pressures of about 5 kPa (about 0.05 atm.) to 10,000 kPa (about 100 atm.) and at a contact time of about 1 minute to 24 hours to form a metallacycle, $L_mNi(1,4-C(R^1)_2C(R^1)_2C(R^2)_2C(R^2)_2-)$. When $(R^2)_2C=C(R^2)_2$ and $(R^1)_2C=C(R^1)_2$ are different alkenes, their preferred mole ratio is normally from about 0.01:1 to 100:1. The mole ratio of alkene to metal employed may vary over a wide range (e.g., from about 0.1:1 to about 100:1). The preferred ratio is normally from about 1:1 to 10:1, but depends to some extent on the particular metal complex and alkene(s) employed, and the desired rate and conversion of $NiL_n$ to metallacycle. Theoretically, a mole ratio of 2 alkenes per metal is required to achieve complete conversion of $NiL_n$ to the metallacycle. It may be desirable to use mole ratios greater than 2 to decrease the time required for metallacycle formation or to ensure complete conversion of the limiting reagent, $NiL_n$, to metallacycle. The excess alkene or its hydrogenation product may then be recovered for recycle or disposal. To avoid this recovery step, it may be desirable to reduce the amount of excess alkene employed to less than 2 per metal, so that the alkene is the limiting reagent and is completely consumed. This results in less than complete conversion of $NiL_n$ to metallacycle, but avoids the presence of excess alkene in the metallacycle product. The exact temperature which is preferred is dependent to a certain extent on the particular metal complex and alkenes being used and the desired rate. Low temperatures may be used, but require relatively long reaction times for practical conversion. Higher temperatures dramatically increase rate, but may in certain cases increase formation of byproducts, which decreases yield. Similarly, low pressures. (e.g., about 100 to 200 kPa) are often satisfactory for carrying out the present invention, but moderate pressures (e.g., 200 to 1000 kPa) can be used to increase reaction rate if desired for economic reasons. Pressures higher than 1000 kPa (about 10 atm.) may be employed if desired, but may often be undesirable for economic reasons. A wide variety of reactor types may be employed, including packed columns, stirred tanks, tubular reactors, etc. At higher temperatures, in the case of a gaseous alkene, the rate of reaction may become limited by mass transfer of the alkene from the gas phase to the liquid phase containing the catalyst, and reactors capable of faster mass transfer will enable faster reaction and shorter contact time. Less effective reactors will require longer contact time. Effective reactors for gas-liquid reactions are well known to those skilled in the art, and are described, for example in Table 2-1 on page 41 of A. Gianetto et al., "Multiphase Chemical Reactors; Theory, Design, Scaleup," Hemisphere Publishing Corp. (1986). The metallacycle is then fed to another reactor and reacted with hydrogen, typically at temperatures from 0 to 200° C., at hydrogen pressures of 100 to 10,000 kPa (about 1 atm. to 100 atm.) and at a contact time of from about 1 minute to about 24 hours to form a $HC(R^1)_2C(R^1)_2C(R^2)_2C(R^2)_2H$ product compound. The hydrogen pressure employed depends to some extent on the particular metallacycle being hydrogenated and the desired rate and conversion. Theoretically at least one mole of $H_2$ per mole of metallacycle is required to achieve complete conversion of metallacycle to product compound, but higher or lower amounts may be employed if desired. As before, the temperature and pressure may be varied depending to a certain extent on the particular metallacycle being hydrogenated and the desired rate. Higher temperatures and pressures result in faster hydrogenation, which leads to a shorter required contact time to reach any given conversion. The product compound is recovered from the reactor by conventional separation techniques such as distillation. Fluorosubstituted hydrocarbons of the formula $HC(R^1)_2C(R^1)_2C(R^2)_2C(R^2)_2H$ may form azeotropes with HF, with olefinic starting materials, with solvents, and with minor hydrofluorocarbon products. Conventional decantation/distillation may be employed if further purification of the hydrofluorocarbons is desired. The $NiL_m$ metal complex liberated during the hydrogenolysis of the $L_mNi(1,4—C(R^1)_2C(R^1)_2C(R^2)_2C(R^2)_2—)$ metallacycle may be recycled to the reactor in which the olefin addition is done. The $NiL_m$ metal complex may be stabilized prior to reaction with the $C(R^1)_2=C(R^1)_2$ and $C(R^2)_2=C(R^2)_2$ olefins by addition of ligands as defined above to the solvent.

Examples of this embodiment of the invention, are represented by the reaction of an $NiL_4$ or an $NiL_3$ complex, in a solvent selected from the group consisting of pentane, hexanes, cyclohexane, benzene, chlorobenzene, toluene, xylene, methyl acetate, methyl formate, and tetrahydrofuran, with an olefin such as tetrafluoroethene. The metallacycle formation reaction is typically done with a mole ratio of alkene to metal of from about 1:1 to about 20:1 at a temperature of from about 50° C. to 150° C. and pressures between about 100 kPa and 800 kPa (about 1 atm. and 8 atm.) with contact times of about 1 minute to 6 hours. The resulting product is a metallacycle of the formula $NiL_2(1,4—(CF_2)_4—)$, dissolved in the solvent.

The $NiL_2(1,4—(CF_2)_4—)$ solution is then reacted with hydrogen, typically at a temperature of from about 80° C. to 180° C. and a hydrogen pressure between about 1000 and 7000 kPa (about 10 atm. and 70 atm.) with a contact time of from about 15 minutes to 8 hours. The hydrogenolysis product, 1,1,2,2,3,3,4,4-octafluorobutane (HFC-338pcc), is separated by conventional techniques such as distillation. The remaining $NiL_2$ fragment which may be stabilized by the presence of excess ligand L, is recycled to the metallacycle formation reactor where it is contacted with additional tetrafluoroethene under the same conditions as described above for the metallacycle formation step.

In a second embodiment of this invention a metal complex of the type $NiL_n$ or a metallacycle of the type $L_mNi(1,4—(CF_2)_4—)$ dissolved in a suitable solvent as described above, is treated with an olefinic compound of the formula $(R^2)_2C=C(R^2)_2$, and another or the same olefinic compound of the formula $(R^1)_2C=C(R^1)_2$, where $R^1$ and $R^2$ are as defined above, and then reacted with hydrogen, typically at a temperature from 0° C. to 200° C., at a hydrogen pressure of from 100 to 10,000 kPa (about 1 atm. to 100 atm.) and at a contact time of 1 hour to 24 hours, such that the mole ratios of $(R^1)_2C=C(R^1)_2$ and $(R^2)_2C=C(R^2)_2$ to metal are from about 0.1:1 to 100:1, to form the $HC(R^1)_2C(R^1)_2C(R^2)_2C(R^2)_2H$ product compound directly. That is, the metallacycle is reacted with hydrogen to give the $HC(R^1)_2C(R^1)_2C(R^2)_2C(R^2)_2H$ product compound and a metal fragment, which can react with additional olefin to form additional metallacycle. In the case where $(R^1)_2C=C(R^1)_2$ and $(R^2)_2C=C(R^2)_2$ are different alkenes and/or where the alkenes are nonsymmetric, it may be possible to form a number of different metallacycles, depending on whether the two alkenes incorporated in the metallacycle are different or the same and/or on the orientation of the two alkene reactants (i.e., head to head, tail to tail, or head to tail). The relative amounts of the two alkenes used can be varied over a wide range, and depend to some extent on the particular metal employed, the differential reactivity of the two alkenes toward that metal, and the particular metallacycle product desired. Normally the preferred ratio of $(R^1)_2C=C(R^1)_2$ to $(R^2)_2C=C(R^2)_2$ is from about 0.01:1 to 100:1. The $HC(R^1)_2C(R^1)_2C(R^2)_2C(R^2)_2H$ product compound(s) may be recovered from the reactor as discussed for the first embodiment.

Examples of this second embodiment of the invention, are represented by the reaction of an $NiL_4$ or an $NiL_3$ complex in a solvent selected from the group consisting of pentane, hexanes, cyclohexane, benzene, chlorobenzene, toluene, xylene, methyl acetate, methyl formate and tetrahydrofuran, with an olefin, such as tetrafluoroethene,-and with hydrogen at a temperature of from about 80° C. to about 180° C., at a pressure of from about 1000 to 7000 kPa (about 10 atm. to about 70 atm.) and at a contact time of from about 0.5 hour to about 5 hours. The hydrogenolysis product, 1,1,2, 2,3,3,4,4-octafluorobutane (HFC-338pcc), is separated by conventional techniques such as distillation.

In a third embodiment of this invention, the metal complex, $NiL_n$, is dissolved in an appropriate solvent, and reacted with an olefinic compound of the type $(R^2)_2C=C(R^2)_2$, where $R^2$ is as defined above, at temperatures from $-25°$ C. to $200°$ C., at pressures of from 5 kPa to 10,000 kPa (0.05 atm. to 100 atm.) and at a contact time of 1 minute to 24 hours to form an olefin complex of the type $L_mNi(\eta^2—C(R^2)_2C(R^2)_2)$. Olefin complexes of this type are known (see, e.g., Tolman et al., J. American Chemical Society, Vol. 96, p. 2774 (1974)). Normally for this embodiment two or more $R^2$ groups are other than F. The mole ratio of olefinic compound to metal employed may vary over a wide range, from about 0.1:1 about 100:1. The preferred ratio is from about 0.5:1 to 10:1 and depends to some extent on the particular metal complex and olefinic compound employed, and the desired rate and conversion of $NiL_n$ to olefin complex. Theoretically, a mole ratio of 1 olefin per metal is required to achieve complete conversion of $NiL_n$ to olefin complex. It may be desirable to use mole ratios greater than 1 to decrease the time required for olefin complex formation or to ensure complete conversion of the limiting reagent, $NiL_n$, to olefin complex. The excess olefin or its hydrogenation product may then be recovered for recycle or disposal. To avoid this recovery step, it may be desirable to reduce the amount of olefin employed to less than 1 per metal, so that the olefin is the limiting reagent and is completely consumed. This results in less than complete conversion of $NiL_n$ to olefin complex, but avoids the presence of excess olefin in the olefin complex product. The olefin complex $L_mNi(\eta^2—C(R^2)_2C(R^2)_2)$ can then be reacted (even without purification or isolation of the olefinic complex) with the other olefinic compound of the type $(R^1)_2C=C(R^1)_2$, where $R^1$ is as defined above, in the same or a different reactor to form the metallacycle. Typically, this reaction is accomplished at temperatures from $-25°$ C. to $200°$ C., at pressures of 5 to 10,000 kPa (about 0.05 atm. to 100 atm.) and at a contact time of 1 minute to 24 hours to form a metallacycle $L_mNi(1,4—C(R^1)_2C(R^1)_2C(R^2)_2C(R^2)_2—)$. The mole ratio of olefin to olefin complex employed may vary over a wide range and is typically from about 0.1:1 to about 100:1. The preferred ratio is from about 1:1 to 10:1 and depends to some extent on the particular olefin complex and olefin employed, and the desired rate and conversion of olefin complex to metallacycle. Theoretically, a mole ratio of 1 olefin per metal is required to achieve complete conversion of olefin complex to metallacycle. It may be desirable to use mole ratios greater than 1 to decrease the time required for metallacycle formation or to ensure complete conversion of the limiting reagent, olefin complex, to metallacycle. The excess olefin or its hydrogenation product may then be recovered for recycle or disposal. To avoid this recovery step, it may be desirable to reduce the amount of olefin employed to less than 1 per metal, so that the olefin is the limiting reagent and is completely consumed. This results in less than complete conversion of olefin complex to metallacycle, but avoids the presence of excess olefin in the metallacycle product. The metallacycle $L_mNi(1,4—C(R^1)_2C(R^1)_2C(R^2)_2C(R^2)_2—)$ is then treated with hydrogen in the same or a different reactor at temperatures from $0°$ C. to $200°$ C., at pressures of about 100 to 10,000 kPa (about 1 atm. to 100 atm.) and at a contact time of 1 minute to 24 hours. This embodiment is particularly advantageous when the olefinic compounds $C(R^1)_2=C(R^1)_2$ and $C(R^2)_2=C(R^2)_2$ are different and it is desired to minimize the amounts of metallacycle $L_mNi(1,4—C(R^1)_2C(R^1)_2C(R^1)_2C(R^1)_2—)$ and $L_mNi(1,4—C(R^2)_2C(R^2)_2C(R^2)_2C(R^2)_2—)$ that may be formed when both olefinic compounds are fed to the $NiL_n$ metal complex at the same time. Product separation and catalyst recycle are carried out in the manner described above.

In a fourth embodiment of this invention, a mixture of the metallacyclic compound, $L_mNi(1,4—C(R^1)_2C(R^1)_2C(R^2)_2C(R^2)_2—)$ and at least one reactant selected from the group consisting of olefinic complexes of the type $L_mNi(\eta^2—C(R^1)_2C(R^1)_2)$ and $L_mNi(\eta^2—C(R^2)_2C(R^2)_2)$, and olefinic compounds of the formulas $C(R^2)_2=C(R^2)_2$ and $C(R^1)_2=C(R^1)_2$, may be reacted with hydrogen to produce a product mixture containing in addition to the product compound, $HC(R^1)_2C(R^1)_2C(R^2)_2C(R^2)_2H$, at least one compound selected from the group consisting of $HC(R^2)_2C(R^2)H$ and $HC(R^1)_2C(R^1)_2H$.

The preferred embodiment depends to some extent on the particular metal complex employed and on the relative reactivity of the two alkenes employed. In cases where one alkene is capable of forming a metallacycle on its own, but the other is not (i.e., is less reactive), formation of a mixed metallacycle can be favored by adding more of the less reactive olefin, or by use of embodiment 3, wherein the less reactive olefin can be added first. In cases where both olefins are capable of forming metallacycles on their own, use of embodiment 1 or 2 may be preferable, where the two olefins may be reacted at the same time, with their relative amounts being adjusted to favor formation of the desired metallacycle. In cases where one olefin is capable of forming a stable olefin complex, embodiment 3 may be particularly useful for preparation of mixed metallacycles. Generally speaking, olefins having more fluorine substituents (e.g., three or four) are more reactive than olefins having fewer fluorine substituents (e.g., zero or one).

A noteworthy embodiment of this invention involves the manufacture of $HCF_2CF_2CF_2CF_2H$ by (a) reacting in the liquid phase $F_2C=CF_2$ and a metal complex soluble in the liquid phase of the formula $NiL_n$ to form a metallacycle of the formula

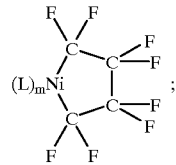

and (b) reacting said cyclic compound with hydrogen. Preferably, L is trineopentylphosphite, n is 4, and m is 2. The $F_2C=CF_2$ and the metal complex may advantageously be reacted, for example, in a solvent selected from the group consisting of pentane, hexanes, cyclohexane, benzene, chlorobenzene, toluene, xylene, methyl acetate, methyl formate and tetrahydrofuran. Also of note are embodiments wherein the $F_2C=CF_2$ and the metallic ligand compound are reacted in $HCF_2CF_2CF_2CF_2H$.

The process of this invention enables production of various compounds of the formula $HC(R^1)_2C(R^1)_2C(R^2)_2C(R^2)_2H$. Of note are product compositions comprising compounds of the formula HCFR$^1$CFR$^1$CHR$^2$CH$_2$R$^2$ where each R$^1$ is selected from the group consisting of H, Cl, F, CN, and OCF$_3$ (provided that at least one R$^1$ is F) and R$^2$ is as defined above. Included are such product compositions comprising compounds where each R$^2$ is selected from the group consisting of H, Cl, F, CN, OCF$_3$, CO$_2$CH$_3$, C$_6$H$_5$, and CF$_3$, provided that at least one R$^2$ is H, and such product compositions comprising compounds where the two R$^2$ groups together form a link selected from the group consisting of —CH$_2$CH$_2$CH$_2$—, —CH$_2$CH$_2$CH$_2$CH$_2$—, —CH$_2$CH$_2$CH(CH$_3$)—, —CH$_2$CH(CH$_3$)CH$_2$—, —C(O)OC(O)—, and norborndiyl (i.e., where the —CHR$^2$CHR$^2$— fragment is derived from cyclopentene, 3-methylcyclopentane, 4-methylcyclopentene, cyclohexene, maleic anhydride, or norbornene). For example, the process of this invention enables production of CHF$_2$CF$_2$CH$_2$CH$_3$ (derived from CF$_2$=CF$_2$ and CH$_2$=CH$_2$); CHF$_2$CH$_2$CH$_2$CHF$_2$ (derived from CF$_2$=CH$_2$); CHClFCF$_2$CClFCHF$_2$ and CHClFCF$_2$CF$_2$CHClF (derived from CClF=CF$_2$); CF$_3$OCHFCF$_2$CF$_2$CHFOCF$_3$, CHF$_2$CF (OCF$_3$)CF$_2$CHFOCF$_3$, and CHF$_2$CF(OCF$_3$)CF(OCF$_3$)CHF$_2$ (derived from CF$_3$OCF=CF$_2$); CH(CN)FCF$_2$CF$_2$CHF(CN), CHF$_2$CF(CN)CF$_2$CHF(CN), and CHF$_2$CF(CN)CF(CN)CHF$_2$ (derived from CF(CN)=CF$_2$); CH$_2$FCH$_2$CF$_2$CHF$_2$ and CH$_3$CHFCF$_2$CHF$_2$ (derived from CH$_2$=CHF and CF$_2$=CF$_2$); CH$_3$CHFCHFCHF$_2$, CH$_2$FCH$_2$CHFCHF$_2$, CH$_2$FCH$_2$CF$_2$CH$_2$F, and CH$_3$CHFCF$_2$CH$_2$F (derived from CH$_2$=CHF and CHF=CF$_2$); CH$_3$CH$_2$CClFCHF$_2$ and CH$_3$CH$_2$CF$_2$CHClF (derived from CH$_2$=CH$_2$ and CClF=CF$_2$); CH$_2$FCH$_2$CClFCHF$_2$, CH$_3$CHFCClFCHF$_2$, and CH$_2$FCH$_2$CF$_2$CHClF (derived from CH$_2$=CHF and CClF=CF$_2$); CH$_3$CH$_2$CF(OCF$_3$)CHF$_2$ and CH$_3$CH$_2$CF$_2$CHFOCF$_3$ (derived from CH$_2$=CH$_2$ and CF$_2$=CFOCF$_3$); CH$_2$FCH$_2$CF(OCF$_3$)CHF$_2$, CH$_3$CHFCF(OCF$_3$)CHF$_2$, CH$_2$FCH$_2$CF$_2$CHFOCF$_3$, and CH$_3$CHFCF$_2$CHFOCF$_3$ (derived from CH$_2$=CHF and CF$_2$=CFOCF$_3$); CH$_2$ClCH$_2$CClFCHF$_2$, CH$_3$CHClCClFCHF$_2$, and CH$_2$ClCH$_2$CF$_2$CHClF (derived from CH$_2$=CHCl and CClF=CF$_2$); CH$_2$ClCH$_2$CF$_2$CHF$_2$ and CH$_3$CHClCF$_2$CHF$_2$ (derived from CH$_2$=CHCl and CF$_2$=CF$_2$); CH$_3$CHClCHFCHF$_2$, CH$_2$ClCH$_2$CHFCHF$_2$, CH$_2$ClCH$_2$CF$_2$CH$_2$F, and CH$_3$CHClCF$_2$CH$_2$F (derived from CH$_2$=CHCl and CHF=CF$_2$); CH$_2$ClCH$_2$CF(OCF$_3$)CHF$_2$, CH$_3$CHClCF(OCF$_3$)CHF$_2$, CH$_2$ClCH$_2$CF$_2$CHFOCF$_3$, and CH$_3$CHClCF$_2$CHFOCF$_3$ (derived from CH$_2$=CHCl and CF$_2$=CFOCF$_3$); CH$_3$CH(CN)CF$_2$CHF$_2$ and CH$_2$CNCH$_2$CF$_2$CHF$_2$ (derived from CH$_2$=CHCN and CF$_2$=CF$_2$); CH$_3$CH(CO$_2$CH$_3$)CF$_2$CHF$_2$ and CH$_3$OC(O)CH$_2$CH$_2$CF$_2$CHF$_2$ (derived from CH$_2$=CHCO$_2$CH$_3$ and CF$_2$=CF$_2$); C$_6$H$_5$CH$_2$CH$_2$CF$_2$CHF$_2$ and CH$_3$CH(C$_6$H$_5$)CF$_2$CHF$_2$ (derived from CH$_2$=CHC$_6$H$_5$ and CF$_2$=CF$_2$); CF$_3$CH$_2$CH$_2$CF$_2$CHF$_2$ and CH$_3$CH(CF$_3$)CF$_2$CHF$_2$ (derived from CH$_2$=CHCF$_3$ and CF$_2$=CF$_2$); CH$_2$CNCH(CN)CF$_2$CHF$_2$ (derived from cis- or trans-CHCN=CHCN and CF$_2$=CF$_2$); and

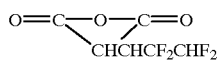

(derived from maleic anhydride and

Other compounds which may be made by the process of this invention include CHF$_2$CF$_2$CF$_2$CHF$_2$ (derived from CF$_2$=CF$_2$); CHF$_2$CClFCClFCHF$_2$ (derived from CClF=CF$_2$); CH$_2$FCF$_2$CHFCHF$_2$, CH$_2$FCF$_2$CF$_2$CH$_2$F, and CHF$_2$CHFCHFCHF$_2$ (derived from CHF=CF$_2$); CHF$_2$CH$_2$CF$_2$CH$_3$ and CH$_3$CF$_2$CF$_2$CH$_3$ (derived from CH$_2$=CF$_2$); CH$_3$CF$_2$CF$_2$CHF$_2$ and CHF$_2$CH$_2$CF$_2$CHF$_2$ (derived from CF$_2$=CH$_2$ and CF$_2$=CF$_2$); CH$_3$CHFCF$_2$CHClF (derived from CH$_2$=CHF and CClF=CF$_2$); and CH$_3$CHClCF$_2$CHClF (derived from CH$_2$=CHCl and CClF=CF$_2$).

Of note are mixtures of two or more product compounds (e.g., a mixture of CHF$_2$CF$_2$CF$_2$CHF$_2$ and CH$_3$CH$_2$CF$_2$CF$_2$H or a mixture of CHF$_2$CF$_2$CF$_2$CHF$_2$ and CH$_2$FCF$_2$CF$_2$CF$_2$H) which can themselves be used for cleaning compositions, either alone or in further combination with other solvents. Product compounds such as HCF$_2$CF$_2$CF$_2$CF$_2$H are also considered useful either alone or in combination with other conventional ingredients (e.g., hydrofluorocarbons, stabilizers, etc.) as agents for fire extinguishants, refrigerants, heat transfer media, foam expansion compositions, aerosol propellants, power cycle working fluids, and sterilant gas carriers.

Compounds of this invention include those of the formula L$_2$Ni(1,4—CR$^1$$_2$CR$^1$$_2$CR$^2$$_2$CR$^2$$_2$—) where R$^1$, R$^2$ and L are defined as indicated above. Of note are compounds where at least three R$^1$ groups are F and at least one R$^2$ group is not F. Preferred compounds of this type include those of the formula

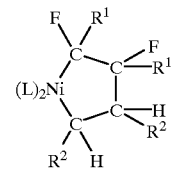

where each R$^1$ is selected from the group consisting of H, Cl, F, OCF$_3$, and CN, provided that at least one R$^1$ is F, and each R$^2$ is selected as indicated above. Preferred compounds of this type also include compounds where each R$^2$ is selected from the group consisting of H, Cl, F, CN, CF$_3$, —C$_6$H$_5$, and CO$_2$CH$_3$, provided that at least one R$^2$ is H; and compounds where each R$^1$ and R$^2$ is F (subject to the indicated proviso).

Examples include L$_2$Ni(1,4—CF$_2$CF$_2$CH$_2$CH$_2$—) (which may be derived from CH$_2$=CH$_2$ and CF$_2$=CF$_2$); L$_2$Ni(1,4—CF$_2$CH$_2$CH$_2$CF$_2$—), L$_2$Ni(1,4—CH$_2$CF$_2$CF$_2$CH$_2$—), and L$_2$Ni(1,4—CF$_2$CH$_2$CF$_2$CH$_2$—) (which may be derived from CF$_2$=CH$_2$); L$_2$Ni(1,4—CClFCF$_2$CClFCF$_2$—), L$_2$Ni(1,4—CClFCF$_2$CF$_2$CClF—), and L$_2$Ni(1,4—CF$_2$CClFCClFCF$_2$—) (which may be derived from CClF=CF$_2$); L$_2$Ni(1,4—(CF$_3$O)CFCF$_2$CF$_2$CF(OCF$_3$)—), L$_2$Ni(1,4—CF$_2$CF(OCF$_3$)CF$_2$CF(OCF$_3$)—), and L$_2$Ni(1,4—CF$_2$CF(OCF$_3$)CF(OCF$_3$)CF$_2$—) (which may be derived from CF$_3$OCF=CF$_2$); L$_2$Ni(1,4—C(CN)FCF$_2$CF$_2$CF(CN)—), L$_2$Ni(1,4—CF$_2$CF(CN)CF$_2$CF(CN)—), and L$_2$Ni(1,4—CF$_2$CF(CN)CF(CN)CF$_2$—) (which may be derived from CF(CN)=CF$_2$); L$_2$Ni(1,4—CHFCH$_2$CF$_2$CF$_2$—) and L$_2$Ni(1,4—CH$_2$CHFCF$_2$CF$_2$—) (which may be derived from CH$_2$=CHF and CF$_2$=CF$_2$); L$_2$Ni(1,4—CH$_2$CHFCHFCF$_2$—), L$_2$Ni(1,4—CHFCH$_2$CHFCF$_2$—), L$_2$Ni(1,4—CHFCH$_2$CF$_2$CHF—), and L$_2$Ni(1,4—CH$_2$CHFCF$_2$CHF—) (which may be derived from CH$_2$=CHF and CHF=CF$_2$); L$_2$Ni(1,4—CH$_2$CH$_2$CClFCF$_2$—) and L$_2$Ni(1,4—CH$_2$CH$_2$CF$_2$CClF—) (which may be derived from CH$_2$=CH$_2$ and CClF=CF$_2$); L$_2$Ni(1,4—CHFCH$_2$CClFCF$_2$—), L$_2$Ni(1,4—CH$_2$CHFCClFCF$_2$—), L$_2$Ni(1,4—CHFCH$_2$CF$_2$CClF—), and L$_2$Ni(1,4—CH$_2$CHFCF$_2$CClF—) (which may be derived from CH$_2$=CHF and CClF=CF$_2$); L$_2$Ni(1,4—CH$_2$CH$_2$CF(OCF$_3$)CF$_2$—) and L$_2$Ni(1,4—CH$_2$CH$_2$CF$_2$CF (OCF$_3$)—) (which may be derived from CH$_2$=CH$_2$ and CF$_2$=CFOCF$_3$); L$_2$Ni(1,4—CHFCH$_2$CF(OCF$_3$)CF$_2$—), L$_2$Ni(1,4—CH$_2$CHFCF(OCF$_3$)CF$_2$—), L$_2$Ni(1,4—CHFCH$_2$CF$_2$CF(OCF$_3$)—), and L$_2$Ni(1,4—CH$_2$CHFCF$_2$CF(OCF$_3$)—) (which may be derived from CH$_2$=CHF and CF$_2$=CFOCF$_3$); L$_2$Ni(1,4—CHClCH$_2$CClFCF$_2$—), L$_2$Ni(1,4—CH$_2$CHClCClFCF$_2$—), L$_2$Ni(1,4—CHClCH$_2$CF$_2$CClF—), and L$_2$Ni(1,4—CH$_2$CHClCF$_2$CClF—) (which may be derived from CH$_2$=CHCl and CClF=CF$_2$); L$_2$Ni(1,4—CHClCH$_2$CF$_2$CF$_2$—) and L$_2$Ni(1,4—CH$_2$CHClCF$_2$CF$_2$—) (which may be derived from CH$_2$=CHCl and CF$_2$=CF$_2$); L$_2$Ni(1,4—CH$_2$CHClCHFCF$_2$—), L$_2$Ni(1,4—CHClCH$_2$CHFCF$_2$—), L$_2$Ni(1,4—CHClCH$_2$CF$_2$CHF—), and L$_2$Ni(1,4—CH$_2$CHClCF$_2$CHF—) (which may be derived from CH$_2$=CHCl and CHF=CF$_2$); L$_2$Ni(1,4—CHClCH$_2$CF (OCF$_3$) CF$_2$—) L$_2$Ni(1,4—CH$_2$CHClCF (OCF$_3$)CF$_2$—), L$_2$Ni(1,4—CHClCH$_2$CF$_2$CHF(OCF$_3$)—), and L$_2$Ni(1,4—CH$_2$CHClCF$_2$CF(OCF$_3$)—) (which may be derived from CH$_2$=CHCl and CF$_2$=CFOCF$_3$); L$_2$Ni(1,4—CH$_2$CH(CN)CF$_2$CF$_2$—) and L$_2$Ni(1,4—CH(CN) CH$_2$CF$_2$CF$_2$) (which may be derived from CH$_2$=CHCN and CF$_2$=CF$_2$); L$_2$Ni(1,4—CH$_2$CH(CO$_2$CH$_3$)CF$_2$CF$_2$-) and L$_2$Ni(1,4—CH(CO$_2$CH$_3$)CH$_2$CF$_2$CF$_2$—) (which may be derived from CH$_2$=CHCO$_2$CH$_3$ and CF$_2$=CF$_2$); L$_2$Ni (1,4—(C$_6$H$_5$)CHCH$_2$CF$_2$CF$_2$—) and L$_2$Ni(1,4—CH$_2$CH (C$_6$H$_5$)CF$_2$CF$_2$—) (which may be derived from CH$_2$=CHC$_6$H$_5$ and CF$_2$=CF$_2$); L$_2$Ni (1,4—(CF$_3$) CHCH$_2$CF$_2$CF$_2$) and L$_2$Ni(1,4—CH$_2$CH(CF$_3$)CF$_2$CF$_2$—) (which may be derived from CH$_2$=CHCF$_3$ and CF$_2$=CF$_2$).

Additional preferred compounds include those of the formula indicated above where each R$^1$ is selected from the group consisting of H, Cl, F, OCF$_3$, and CN, provided that at least one R$^1$ is F, and where both R$^2$s are CN, or where both R$^2$s together may comprise a link selected from the group —CH$_2$CH$_2$CH$_2$—, —CH$_2$CH$_2$CH$_2$CH$_2$—, —CH$_2$CH$_2$CH(CH$_3$)—, —CH$_2$CH(CH$_3$)CH$_2$—, C(O)OC (O), and

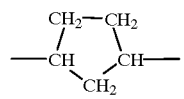

(that is, where the C(R$^2$)HC(R$^2$)H fragment is derived from the olefinic compounds, cyclopentene, 3-methyl cyclopentene, 4-methyl cyclopentene, cyclohexene, maleic anhydride, or norbornene).

Examples include L$_2$Ni(1,4—CH(CN)CH(CN) CF$_2$CF$_2$—) (which may be derived from cis- or trans-CHCN=CHCN and CF$_2$=CF$_2$);

(which may be derived from cyclopentene and CF$_2$=CF$_2$);

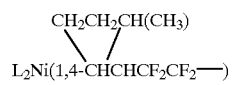

(which may be derived from 3-methyl cyclopentene and CF$_2$=CF$_2$);

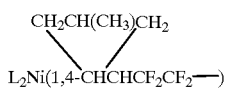

(which may be derived from 4-methyl cyclopentene and CF$_2$=CF$_2$);

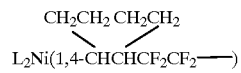

(which may be derived from cyclohexene and CF$_2$=CF$_2$),

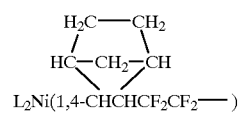

(which may be derive from maleic anhydride and CF$_2$=CF$_2$); and

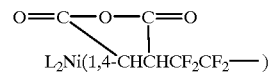

(which may be derived from norbornene and CF$_2$=CF$_2$). Also of note are compounds where each R$^1$ is F and each R$^2$ is H.

Of particular note is the preparation of Ni(P(OCH$_2$C (CH$_3$)$_2$(R$^5$))$_3$)$_4$ by the reaction of elemental Ni, preferably nickel powder, with P(OCH$_2$C(CH$_3$)$_2$(R$^5$))$_3$ optionally with the use of a halogenated catalyst, using a procedure similar to that described in U.S. Pat. No. 3,903,120.

Novel nickel starting materials for the process of this invention include compounds of the formula NiL$_4$ (e.g., Ni(trineopentylphosphite)$_4$).

Practice of the invention will become further apparent from the following non-limiting examples.

EXAMPLES

Nuclear Magnetic Resonance (NMR) Data
Abbreviations s singlet
d doublet

EXAMPLE 1

Preparation of Ni(Trineopentylphosphite)$_4$ by the Reaction of Ni(Cyclooctadiene)$_2$ with Trineopentylphosphite Solid Ni(Cyclooctadiene)$_2$ (5.5 g, 20 mmol) was added in small portions into a stirred solution of trineopentylphosphite (26.32 g, 90 mmol) in 100 mL toluene. The reaction was heated briefly to reflux, then cooled to room temperature, resulting in formation of two phases. Removal of solvent under vacuum gave a white powder. $^{31}$P NMR (C$_6$D$_6$ solution):157.5 (s, NiL$_4$, L=trineopentylphosphite), 139.8 (s, uncoordinated L). The free L is due to the approximately 10% excess used in the preparation.

EXAMPLE 2

Preparation of Ni(Trineopentylphosphite)$_4$ by the Reaction of Ni powder with Trineopentylphosphite A mixture of 3.64 g Ni (62 mmol), 27.6 g trineopentylphosphite (94.4 mmol), 320 g acetonitrile, and 0.1 mmol PCl₃ (added as an acetonitrile solution) was stirred in a 1000 mL flask at reflux for 24 hours. An additional 1 g trineopentylphosphite and 0.4 g PCl₃ was added and reaction continued another 24 hours. The crude product was collected on a frit and extracted with 500 mL hot toluene. Removal of the toluene from the filtrate gave 17.5 g (58% yield) of Ni(trineopentylphosphite)₄ as a greyish-white solid.

EXAMPLE 3

Synthesis of CHF₂CF₂CF₂CHF₂ (HFC-338pcc) using Ni(Trineopentylphosphite)₄

A mixture of 10.98 g NiL₄ (8.94 mmol, L=trineopentylphosphite) and 5.29 g trineopentylphosphite (18.1 mmol) in 15 mL toluene was charged to a 50 cc autoclave. The autoclave was pressurized with 30 psig TFE, then heated to 110° C. After stirring for 3 hours, the TFE pressure was vented. The reactor was purged with helium, heated to 145° C., and pressurized with 300 psig of hydrogen. After 17 hours, the reactor was cooled to 54° C., vented, purged with helium, and heated to 110° C. Once at 110° C., 30 psig TFE was admitted and reaction continued for 3.25 hours. The reaction was cooled and an NMR sample obtained. The ³¹P NMR showed NiL₄ (157.5 ppm, s), uncoordinated trineopentylphosphite (139.7, s), and the L₂Ni(C₄F₈) metallacycle (128.0, broad quintet) in integrated intensity ratio 1:6.1:1.7, indicating that on a molar basis 77% of the nickel is in the form of metallacycle and 23% in the form of NiL₄. The ¹⁹F NMR clearly showed metallacycle (alpha fluorines at −102 ppm, beta fluorines at −137.2) and HFC-338pcc (−131, s; −137.3, d) in molar ratio 1.4:1, along with a trace of residual TFE (−132 ppm, s).

Two additional hydrogenation/TFE reaction cycles were done, stopping after the fourth TFE addition. A ¹⁹F NMR spectrum of the solution showed HFC-338pcc and the L₂Ni(C₄F₈) metallacycle in the ratio 9.4:1. The solvent was removed under vacuum, the residue re-slurried in toluene, and reacted with 30 psig TFE at 120° C. for 5 hours. The ³¹P NMR spectrum of the resulting solution showed NiL₄, uncoordinated trineopentylphosphite, and L₂Ni(C₄F₈) in an integrated ratio 1:4.3:0.56. This data indicated that 53% of the nickel was converted to metallacycle and that the catalyst was still active.

The structure of the L₂Ni(C₄F₈) metallacycle was further confirmed by means of a crystal structure obtained by X-ray diffraction.

EXAMPLE 4

Synthesis of CHF₂CF₂CF₂CHF₂ (HFC-338pcc) using Ni(Trineopentylphosphite)₄

A mixture of 0.2 g NiL₄ (0.163 mmol, L=trineopentylphosphite), 0.4 g trineopentylphosphite (1.37 mmol), and 20 mL toluene (14.8 g) was charged to a 400 mL pressure vessel. The vessel was pressurized with 100 psig TFE and 350 psi H₂, for a total pressure of 450 psig at room temperature. The vessel was sealed and heated to 145° C. with shaking to agitate the contents; the reaction was continued for a total of 44 hours. The reaction was cooled and vented. Then a second charge of 100 psig TFE and 269 psig H₂ was admitted to the vessel, for a total pressure of 369 psig. The reaction was again heated to 145° C. with shaking for another 19–20 hours. The vessel was cooled and vented and 25.01 g liquid product was recovered from the vessel. Analysis by gas chromatography using an external standard showed the composition of the product to be 48% HFC-338pcc, which equates to a turnover number of 367 moles HFC-338pcc/mole Ni.

What is claimed is:

1. A process for the manufacture of a product compound of the formula HC(R¹)₂C(R¹)₂C(R²)₂C(R²)₂H wherein each R¹ is independently selected from the group consisting of H, F, Cl, CN, R, OR, CO₂R, C(O)R, OC(O)R, Rᶠ, ORᶠ, CO₂Rᶠ, C(O)Rᶠ and OC(O)Rᶠ, where R is a hydrocarbyl group and Rᶠ is a C₁ to C₁₀ polyfluoroalkyl group, provided that at least one R¹ is F, and wherein each R² is independently selected from the group consisting of H, F, Cl, CN, R, OR, CO₂R, C(O)R, OC(O)R, Rᶠ, ORᶠ, CO₂Rᶠ, C(O)Rᶠ, OC(O)Rᶠ and difunctional linkages where an R² on each of two adjacent carbon atoms together form a link selected from the group consisting of —CH₂CH₂CH₂—, —CH₂CH₂CH₂CH₂—, —CH₂CH₂CH(CH₃)—, —CH₂CH(CH₃)CH₂—, —C(O)OC(O)—, and norborndiyl, comprising:

reacting a metallacycle of the formula

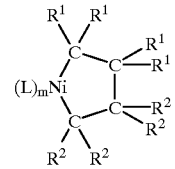

wherein R¹ and R² are as defined above, and wherein each L is a ligand independently selected from the group consisting of a phosphite of the formula P(OR³)₃,

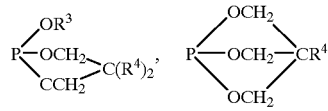

and (R₃O)₂POP(OR₃)₂; each R³ is independently selected the group consisting of CH₂CR⁶R⁷R⁸; each R⁶, R⁷, and R⁸ is independently selected from the group consisting of C₁ to C₁₀ alkyl, benzyl, phenyl, and phenyl substituted with one or more R¹⁰, provided that two of R⁶, R⁷, and R⁸ in a R³ may be co-joined to provide a C₅ to C₇ cycloalkane ring, and that all three of R⁶, R⁷, and R⁸ in an R³ may together form an adamantyl group; each R¹⁰ is independently selected from the group consisting of C₁ to C₄ alkyl, F, Cl, Br, N(R⁹)₂, OR⁹ and CO₂R⁹ where each R⁹ is independently selected from the group consisting of H and C₁ to C₄ alkyl; each R⁴ is independently selected from the group consisting of C₁ to C₄ alkyl; and m is an integer from 1 to 2, with hydrogen.

2. The process of claim 1 wherein the metallacycle is formed by reacting a first olefinic reactant of the formula (R²)₂C═C(R²)₂, a second olefinic reactant of the formula (R¹)₂C═C(R¹)₂, and a metal complex soluble in the liquid phase of the formula NiLₙ, and n is an integer from 2 to 4.

3. A compound of the formula L₂Ni(1,4—CR¹₂CR¹₂CR²₂CR²₂—) wherein each R¹ is independently selected from the group consisting of H, F, Cl, CN, R, OR, CO₂R, C(O)R, OC(O)R, Rᶠ, ORᶠ, CO₂Rᶠ, C(O)Rᶠ and OC(O)Rᶠ, where R is a hydrocarbyl group and Rᶠ is a C₁ to C₁₀ polyfluoroalkyl group, provided that at least one R¹ is F, wherein each R² is independently selected from the group consisting of group H, F, Cl, CN, R, OR, CO₂R, C(O)R, OC(O)R, Rᶠ, ORᶠ, CO₂Rᶠ, C(O)Rᶠ, OC(O)Rᶠ and difunctional linkages where an R² on each of two adjacent carbon atoms together form a link selected from the group consisting of —CH₂CH₂CH₂—, —CH₂CH₂CH₂CH₂—, —$CH_2CH_2CH(CH_3)$—, —$CH_2CH(CH_3)CH_2$—, —$C(O)OC(O)$—, and norborndiyl, and wherein each L is a ligand independently selected from the group consisting of a phosphite of the formula $P(OR^3)_3$,

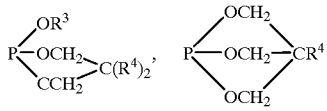

and $(R_3O)_2POP(OR_3)_2$; each $R^3$ is independently selected the group consisting of $CH_2CR^6R^7R^8$; each $R^6$, $R^7$, and $R^8$ is independently selected from the group consisting of $C_1$ to $C_{10}$ alkyl, benzyl, phenyl, and phenyl substituted with one or more $R^{10}$, provided that two of $R^6$, $R^7$, and $R^8$ in a $R^3$ may be co-joined to provide a $C_5$ to $C_7$ cycloalkane ring, and that all three of $R^6$, $R^7$, and $R^8$ in a $R^3$ may together from an adamantyl group; each $R^{10}$ is independently selected from the group consisting of $C_1$ to $C_4$ alkyl, F, Cl, Br, $N(R^9)_2$, $OR^9$ and $CO_2R^9$; each $R^9$ is independently selected from the group consisting of H and $C_1$ to $C_4$ alkyl; each $R^4$ is independently selected from the group consisting of $C_1$ to $C_4$ alkyl.

4. The compound of claim 3 selected from the group consisting of $L_2Ni(1,4—CF_2CF_2CH_2CH_2—)$, $L_2Ni(1,4—CF_2CH_2CH_2CF_2—)$, $L_2Ni(1,4—CH_2CF_2CF_2CH_2—)$, $L_2Ni(1,4—CF_2CH_2CF_2CH_2—)$, $L_2Ni(1,4—CClFCF_2CClFCF_2—)$, $L_2Ni(1,4—CClFCF_2CF_2CClF—)$, $L_2Ni(1,4—CF_2CClFCClFCF_2—)$, $L_2Ni(1,4—(CF_3O)CFCF_2CF_2CF(OCF_3)—)$, $L_2Ni(1,4—CF_2CF(OCF_3)CF_2CF(OCF_3)—)$, $L_2Ni(1,4—CF_2CF(OCF_3)CF(OCF_3)CF_2—)$, $L_2Ni(1,4—C(CN)FCF_2CF_2CF(CN)—)$, $L_2Ni(1,4—CF_2CF(CN)CF_2CF(CN)—)$, $L_2Ni(1,4—CF_2CF(CN)CF(CN)CF_2—)$, $L_2Ni(1,4—CHFCH_2CF_2CF_2—)$, $L_2Ni(1,4—CH_2CHFCF_2CF_2—)$, $L_2Ni(1,4—CH_2CHFCHFCF_2—)$, $L_2Ni(1,4—CHFCH_2CHFCF_2—)$, $L_2Ni(1,4—CHFCH_2CF_2CHF—)$, $L_2Ni(1,4—CH_2CHFCF_2CHF—)$, $L_2Ni(1,4—CH_2CH_2CClFCF_2—)$, $L_2Ni(1,4—CH_2CH_2CF_2CClF—)$, $L_2Ni(1,4—CHFCH_2CClFCF_2—)$, $L_2Ni(1,4—CH_2CHFCClFCF_2—)$, $L_2Ni(1,4—CHFCH_2CF_2CClF—)$, $L_2Ni(1,4—CH_2CHFCF_2CClF—)$, $L_2Ni(1,4—CH_2CH_2CF(OCF_3)CF_2$, $L_2Ni(1,4—CH_2CH_2CF_2CF(OCF_3)—)$, $L_2Ni(1,4—CHFCH_2CF(OCF_3)CF_2—)$, $L_2Ni(1,4—CH_2CHFCF(OCF_3)CF_2—)$, $L_2Ni(1,4—CHFCH_2CF_2CF(OCF_3)—)$, $L_2Ni(1,4—CH_2CHFCF_2CF(OCF_3)—)$, $L_2Ni(1,4—CHClCH_2CClFCF_2—)$, $L_2Ni(1,4—CH_2CHClCClFCF_2—)$, $L_2Ni(1,4—CHClCH_2CF_2CClF—)$, $L_2Ni(1,4—CH_2CHClCF_2CClF—)$, $L_2Ni(1,4—CHClCH_2CF_2CF_2—)$, $L_2Ni(1,4—CH_2CHClCF_2CF_2—)$, $L_2Ni(1,4—CH_2CHClCHFCF_2—)$, $L_2Ni(1,4—CHClCH_2CHFCF_2—)$, $L_2Ni(1,4—CHClCH_2CF_2CHF—)$, $L_2Ni(1,4—CH_2CHClCF_2CHF—)$, $L_2Ni(1,4—CHClCH_2CF(OCF_3)CF_2—)$, $L_2Ni(1,4—CH_2CHClCF(OCF_3)CF_2—)$, $L_2Ni(1,4—CHClCH_2CF_2CHF(OCF_3)—)$, $L_2Ni(1,4—CH_2CHClCF_2CF(OCF_3)—)$, $L_2Ni(1,4—CH_2CHCICF_2CF(OCF_3)—)$, $L_2Ni(1,4—CH_2CH(CN)CF_2CF_2—)$, $L_2Ni(1,4—CH(CN)CH_2CF_2CF_2—)$, $L_2Ni(1,4—CH_2CH(CO_2CH_3)CF_2CF_2—)$, $L_2Ni(1,4—CH(CO_2CH_3)CH_2CF_2CF_2—)$, $L_2Ni(1,4—(C_6H_5)CHCH_2CF_2CF_2—)$, $L_2Ni(1,4—CH_2CH(C_6H_5)CF_2CF_2—)$, $L_2Ni(1,4—(CF_3)CHCH_2CF_2CF_2—)$, $L_2Ni(1,4—CH_2CH(CF_3)CF_2CF_2—)$ $L_2Ni(1,4—$

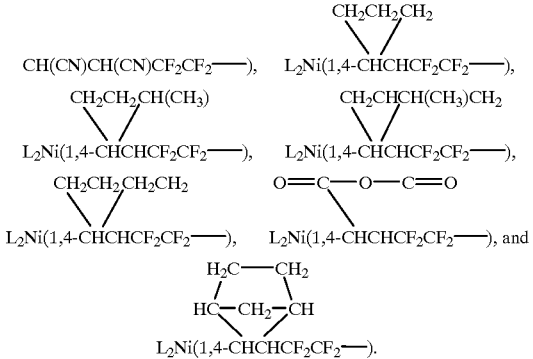

5. A nickel compound of the formula, $NiL_4$ wherein L is selected from the group consisting of phosphites of the formula $P(OR^3)_3$, phosphites of the formula

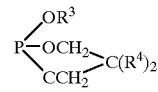

and phosphites of the formula $(R_3O)_2POP(OR_3)_2$, wherein each $R^3$ is independently selected the group consisting of $CH_2CR^6R^7R^8$; each $R^6$, $R^7$, and $R^8$ is independently selected from the group consisting of $C_1$ to $C_{10}$ alkyl, benzyl, phenyl, and phenyl substituted with one or more $R^{10}$, provided that two of $R^6$, $R^7$, and $R^8$ in an $R^3$ may be co-joined to provide a $C_5$ to $C_7$ cycloalkane ring, and that all three of $R^6$, $R^7$, and $R^8$ in an $R^3$ may together form an adamantyl group; each $R^{10}$ is independently selected from the group consisting of $C_1$ to $C_4$ alkyl, F, Cl, Br, $N(R^9)_2$, $OR^9$ and $CO_2R^9$; each $R^9$ is independently selected from the group consisting of H and $C_1$ to $C_4$ alkyl; and each $R^4$ is independently selected from the group consisting of $C_1$ to $C_4$ alkyl.

6. A compound of claim 5 which is $Ni(trinecpentylphomphite)_4$.

* * * * *